US00PP26556P3

(12) United States Plant Patent
Jacobs

(10) Patent No.: US PP26,556 P3
(45) Date of Patent: Mar. 29, 2016

(54) ***CHRYSANTHEMUM* PLANT NAMED 'ZANMUPERFECOR'**

(50) Latin Name: ***Chrysanthemum×morifolium* Ramat.**
Varietal Denomination: Zanmuperfecor

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 192 days.

(21) Appl. No.: 13/998,969

(22) Filed: Dec. 30, 2013

(65) Prior Publication Data

US 2015/0189815 P1 Jul. 2, 2015

(51) Int. Cl.
*A01H 5/00* (2006.01)

(52) U.S. Cl.
USPC ..... Plt./296

(58) Field of Classification Search
USPC ..... Plt./296
See application file for complete search history.

*Primary Examiner* — Keith Robinson
(74) *Attorney, Agent, or Firm* — Steptoe & Johnson LLP

(57) ABSTRACT

A *Chrysanthemum* plant named 'Zanmuperfecor' characterized by its medium sized blooms with bronze ray florets and a dark center, and prolific branching; natural season flowering date September 9-14 (week 37); blooming for a period of 5 weeks.

3 Drawing Sheets

Botanical designation: *Chrysanthemum×morifolium* Ramat.

Cultivar denomination: 'Zanmuperfecor'.

RELATED CULTIVARS

This new plant a mutant obtained from the *Chrysanthemum* plant 'Zanmuperfect' (U.S. Plant Pat. No. 23,015).

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmuperfecor'.'Zanmuperfecor' is a product of a breeding and selection program for outdoor pot mums (garden mums) which had the objective of finding color mutants from existing parent plants. The new plant comprises a whole plant mutation from the *Chrysanthemum* plant named 'Zanmuperfect'. Plants of the new cultivar 'Zanmuperfecor' differ from plants of the parent in the color of the inflorescences; the inflorescences are orange in 'Zanmuperfecor' and pink in 'Zanmuperfect'.

The new and distinct cultivar was discovered and selected as a flowering plant by Henricus Cornelius Maria Jacobs on a cultivated field in Rijsenhout, The Netherlands in 2007. The first act of asexual production of 'Zanmuperfecor' was accomplished when vegetative cuttings from the initial selection in 2007 were propagated further in a controlled environment in Rijsenhout, The Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *Chrysanthemum* (of about 16 weeks) is shown in the accompanying drawings, the color being as nearly true as possible with color photographs of this type.

DESCRIPTION OF THE INVENTION

Figure 1:
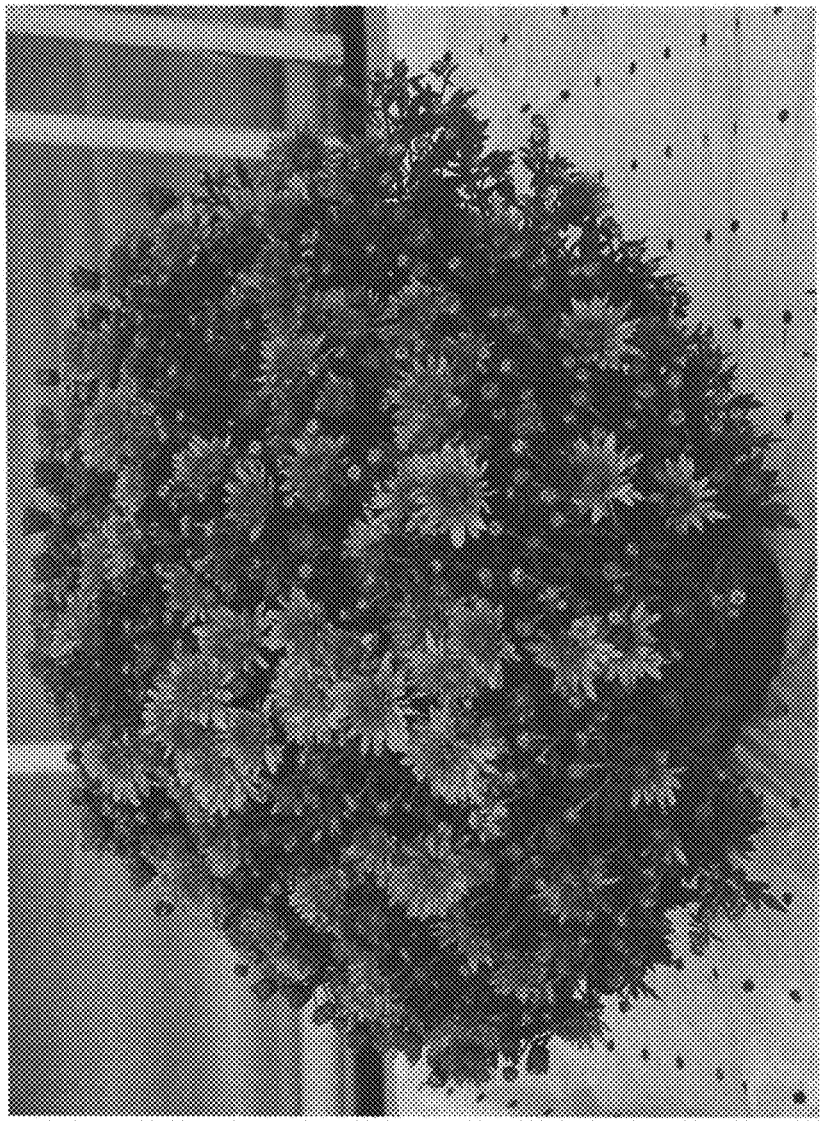
FIG. 1 shows a plant of the cultivar in full bloom.
Figure 2:
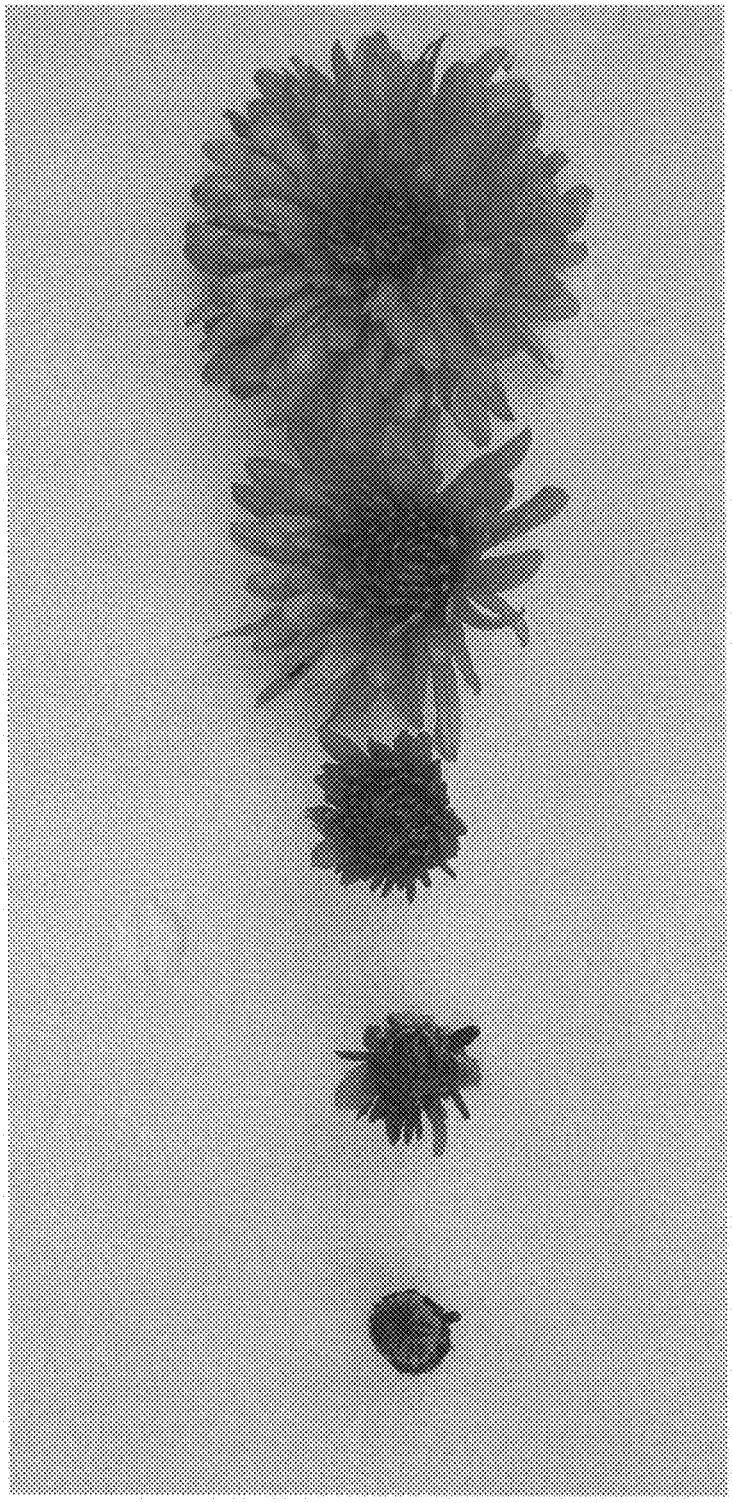
FIG. 2 shows the various stages of bloom of the new cultivar.
Figure 3:
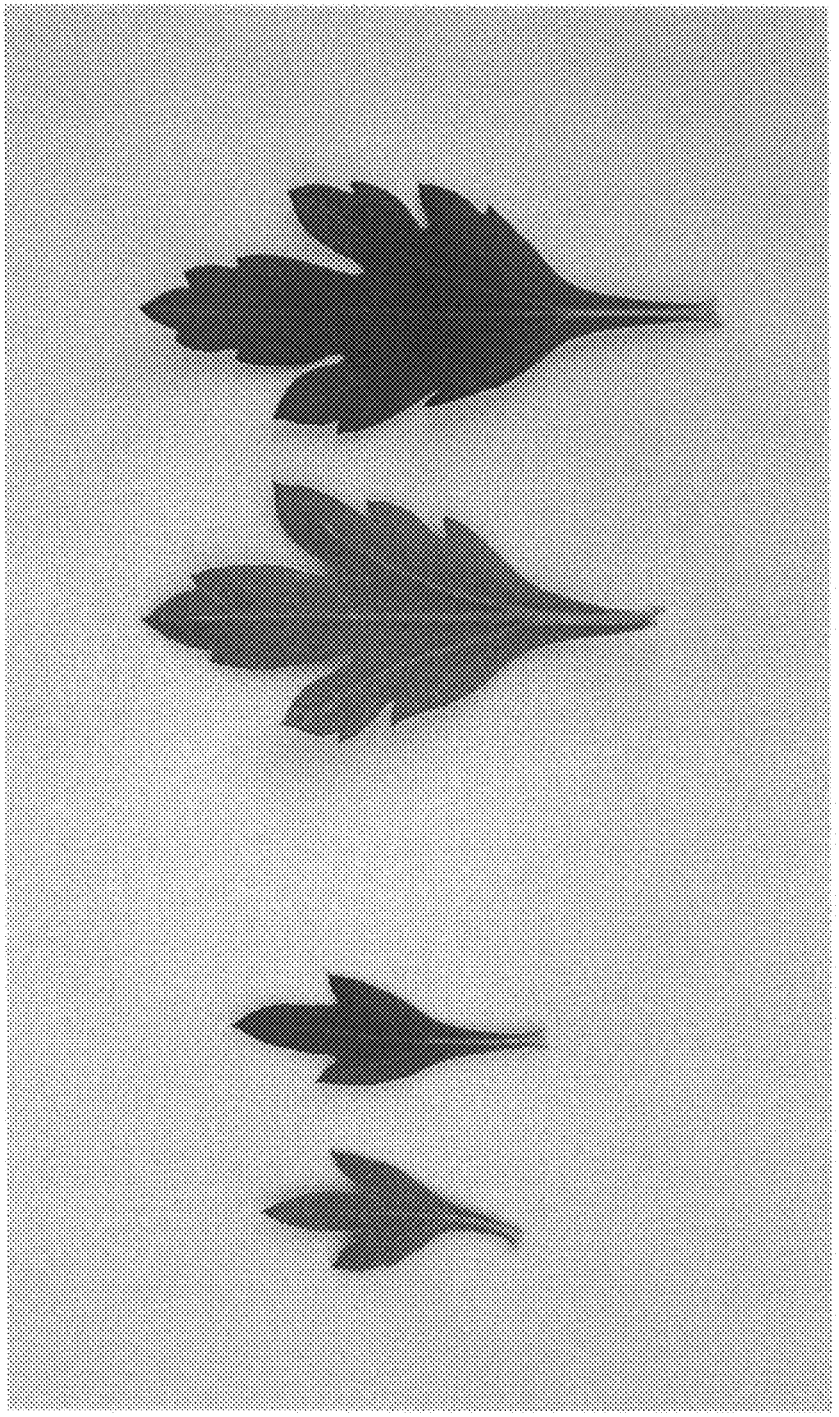
FIG. 3 shows the various stages of foliage of the new cultivar.

The observations and measurements were gathered from plants, in the period of 15 to 22 weeks of age, grown outdoor in Rijsenhout, The Netherlands, under natural day length and temperature and planted in week 23 in 2013 (with a warm summer), receiving drip irrigation. The natural blooming date of this crop was September 9-14 (week 37) . The average height of the plants was 30 cm. No growth retardants were used. No tests were done on disease or insect resistance or susceptibility. No tests were done on cold or drought tolerance. This new variety produces medium sized blooms with bronze ray florets and a dark center blooming for a period of 5 weeks.

From the cultivars known to the inventor the most similar existing cultivar in comparison to 'Zanmuperfecor' is its parent 'Zanmuperfect' (U.S. Plant Pat. No. 23,015). When 'Zanmuperfecor' and 'Zanmuperfect' are being compared the following differences are noticed. (1). Color center inflorescences. And (2). Ray-floret color. (1). Inflorescences of 'Zanmuperfecor' have an orange center, while those of 'Zanmuperfect' have a red center. (2). Ray-florets of 'Zanmuperfecor' are bronze, while those of 'Zanmuperfect' are pink.

The following is a description of the plant and characteristics that distinguish 'Zanmuperfecor' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmuperfecor'

| | |
|---|---|
| **Bud** | |
| Size: | Small; cross-section 6-8 mm, height 4-5 mm |
| Shape: | Round |
| Texture: | Pubescent |
| Outside color: | Greyed-green 191A |
| **Phyllaries** | |
| Number: | 21-22, arranged in 3 rows |
| Shape: | Elliptic |
| Apex: | Acute |
| Base: | Truncate |
| Margin: | Entire |
| Color: | Upper side: Green 137A<br>Lower side: Green N138C |
| Length and width: | 8-10 mm; 2-3 mm |
| Texture: | Pubescent |
| **Inflorescences** | |
| Type: | Double |
| Height: | 2 cm |
| Diameter: | 5.5 cm |
| Peduncle length: | 9.5-11 cm |
| Peduncle color: | Green 138C |
| Peduncle diameter: | 2 mm |
| Peduncle texture: | Pubescent |
| Peduncle strength: | Weak |
| Number per branch: | About. 5-7 inflorescences |
| Duration of flowering: | 5 weeks |
| Seeds: | Produced in small quantities, ovate, Greyed-brown 199A, length 1.5 mm, diameter 0.5 mm; structure: rough with ribs |
| Fragrance: | Faint *chrysanthemum* odor |
| **Color inflorescences** | |
| Center of inflorescence: | Immature stage: Greyed-orange 173A; Mature stage: Greyed-orange 173A |
| Color of upper side of ray florets: | Greyed-orange 166C |
| Color of lower side of ray florets: | Greyed-orange 165C |
| Tonality from distance: | A garden *mum* with bronze blooms and a dark center |
| Color of ray florets after aging of the plant: | Greyed-orange 164C |
| **Ray florets** | |
| Type: | Ligulate |
| Texture: | Upper and lower side smooth |
| Number: | 170-180 |
| Shape: | elliptic |
| Apex: | dentate |
| Base: | acute |
| Cross-section: | flat |
| Longitudinal axis: | straight |
| Length of corolla tube: | 3-4 mm |
| Diameter corolla tube: | 1 mm |
| Ray floret margin: | Entire |
| Ray floret length: | 1.7-2.7 cm |
| Ray floret width: | 2-4 mm |
| Ratio length/width: | High |
| Disc florets | absent |
| **Receptacle** | |
| Color: | Yellow-green 145D |
| Shape: | Domed raised |
| Height: | 3 mm |
| Diameter: | 3 mm |
| **Reproductive Organs** | |
| Androecium: | absent |
| Pollen: | absent |
| Gynoecium: | Present on ray florets |
| Style color: | Yellow-green 154C |
| Style length: | 4 mm |

TABLE 1-continued

Botanical Description of *Chrysanthemum* × *morifolium* Ramat. 'Zanmuperfecor'

| | |
|---|---|
| Stigma color: | Yellow 7A |
| Stigma width: | 1 mm |
| Ovary: | Enclosed in calyx; color: Yellow-green 149D |
| **Plant** | |
| Type: | Bushy |
| Growth habit: | Spherical shape |
| Growth rate: | Medium to high |
| Height: | 30 cm |
| Width: | 50 cm |
| Stem color: | Greyed-brown 199A |
| Stem strength: | weak |
| Stem brittleness: | brittle |
| Stern anthocyanin coloration: | absent |
| Internode length: | 1-2.5 cm |
| Length of lateral branch: | From top to bottom 25 cm |
| Lateral branch color: | Green 137 C |
| Lateral branch, attachment: | Weak |
| Lateral branch diameter: | 2.5 mm |
| Lateral branch texture: | Pubescent with ribs |
| Branching (average number of lateral branches): | Dense with 8 breaks after pinching |
| Natural season blooming date: | September 9-14 (week 37) in Rijsenhout, The Netherlands |
| Roots—habits: | Fine, freely branching |
| Roots—color: | White 155D |
| **Foliage** | |
| Glossiness: | Leaf upper side: very weak<br>Leaf lower side: absent |
| Leaf color: | Upper side: Green 139A<br>Lower side: Green 138A |
| Color midvein: | Upper side: Yellow-green 147D<br>Lower side: Yellow-green 148D |
| Size: | Small; length 3.-4.5 cm, width 1.8-2.5 cm |
| Quantity (number per lateral branches): | 28-30 |
| Shape: | Elliptic to broadly elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |
| Shape of base: | Truncate to asymmetric |
| Apex: | Mucronulate |
| Petiole attitude: | Moderately upwards |
| Petiole length: | 0.8-1 cm |
| Petiole diameter: | 1.5-2 mm |
| Petiole color: | Yellow-green 147D |
| Stipule: | Small, about 1 cm |

TABLE 2

Differences with the comparison variety, when grown under identical conditions

| | 'Zanmuperfecor' | 'Zanmuperfect' |
|---|---|---|
| Color ray-florets | Greyed-orange 166C | Red-purple 70D |
| Color center inflorescences | Greyed-orange 173A | Red 51A |

I claim:

1. A new and distinct *Chrysanthemum* plant named 'Zanmuperfecor' as described and illustrated.

* * * * *